(12) United States Patent
Bonrath et al.

(10) Patent No.: US 6,743,615 B2
(45) Date of Patent: Jun. 1, 2004

(54) PROCESS FOR THE MANUFACTURE OF A VITAMIN E INTERMEDIATE

(75) Inventors: Werner Bonrath, Freiburg (DE); Detlef Eisenkraetzer, Penzberg (DE); Valerie Enjolras, St. Jean Bonnefonds (FR); Reinhard Karge, Staufen (DE); Thomas Netscher, Bad Krozingen (DE); Michael Schneider, Frick (CH)

(73) Assignee: Roche Vitamins, Inc., Parsippany, NJ (US)

( * ) Notice: Subject to any disclaimer, the term of this patent is extended or adjusted under 35 U.S.C. 154(b) by 0 days.

(21) Appl. No.: 10/078,789

(22) Filed: Feb. 19, 2002

(65) Prior Publication Data

US 2002/0161246 A1 Oct. 31, 2002

(30) Foreign Application Priority Data

Feb. 21, 2001 (EP) ............................................. 01104141

(51) Int. Cl.$^7$ .............................. C12N 9/14; C12N 9/16; C12N 9/20; C12N 9/30
(52) U.S. Cl. ...................... 435/198; 435/195; 435/196; 435/203
(58) Field of Search .................................. 435/195, 196, 435/198, 203

(56) References Cited

U.S. PATENT DOCUMENTS 5,445,951 A * 8/1995 Palmer et al. .............. 435/100

FOREIGN PATENT DOCUMENTS

CS 239442 * 1/1986

OTHER PUBLICATIONS

The CABRI consortium 1999–2003, http//www, cabri. Org/.*
Ciuffreda, P., et al., "Regioselective Hydrolysis of Diacetoxynaphthalenes Catalyzed by Pseudomonas sp. Lipase in an Organic Solvent", *Tetrahedron*, v. 56, pp. 317–321 (2000).
Patent Abstracts of Japan of JP 08119958 (1996).
Chemical Abstracts No. XP–002201206.

* cited by examiner

*Primary Examiner*—Christopher R. Tate
*Assistant Examiner*—Kailash C. Srivastava
(74) *Attorney, Agent, or Firm*—Bryan Cave LLP

(57) ABSTRACT

The present invention is a process for converting trimethylhydroquinone diacetate (TMHQ-DA) into trimethylhydroquinone-1-monoacetate (TMHQ-1-MA) by contacting TMHQ-DA with a lipase to effect an enzymatic monosaponification of the TMHQ-DA. Also provided are methods of making (all-rac)-α-tocopherol and (all-rac)-α-tocopherol acetate.

7 Claims, No Drawings

PROCESS FOR THE MANUFACTURE OF A VITAMIN E INTERMEDIATE

FIELD OF THE INVENTION

The present invention relates to a process for converting trimethyl-hydroquinone diacetate (TMHQ-DA) into trimethylhydroquinone-1-monoacetate (TMHQ-1-MA) by contacting TMHQ-DA with a lipase to effect an enzymatic monosaponification of the TMHQ-DA. Methods of making (all-rac)-α-tocopherol and (all-rac)-α-tocopherol acetate are also provided.

BACKGROUND OF THE INVENTION

The major commercial form of vitamin E is its acetate derivative, synthesized by acetylation of (all-rac)-α-tocopherol, e.g. with acetic anhydride.

Industrial syntheses of (all-rac)-α-tocopherol are based on the condensation of trimethylhydroquinone (TMHQ) with isophytol, phytol or a derivative thereof, such as a phytyl halide. TMHQ is normally obtained from 2,3,6-trimethylphenol which is expensive, however, and acidic catalysts have to be used for the condensation of the TMHQ with isophytol, phytol or a derivative thereof, such as a phytyl halide.

Alternatively, (all-rac)-α-tocopherol acetate can be synthesized by condensing trimethylhydroquinone-1-monoacetate (TMHQ-1-MA) with isophytol or an equivalent thereof, i.e. e.g. phytol or a derivative thereof, such as a phytyl halide. The TMHQ-1-MA used in this alternative synthesis can be obtained from the much less expensive α-isophorone via ketoisophorone and trimethylhydroquinone diacetate (TMHQ-DA), the latter having to undergo an absolutely regioselective mono-deacetylation which is difficult to achieve by methods known from literature (e.g. by treatment with aqueous alkaline bases), however.

SUMMARY OF THE INVENTION

One embodiment of the present invention is a process for converting trimethylhydroquinone diacetate (TMHQ-DA) into trimethylhydroquinone-1-monoacetate (TMHQ-1-MA) by contacting TMHQ-DA with a lipase to effect an enzymatic monosaponification of the TMHQ-DA.

Another embodiment of the present invention is a process of making (all-rac)-α-tocopherol acetate having the steps of reacting trimethylhydroquinone diacetate (TMHQ-DA) with a lipase to form trimethylhydroquinone-1-monoacetate (TMHQ-1-MA), followed by reacting the TMHQ-1-MA with isophytol or an equivalent thereof to form (all-rac)-α-tocopherol acetate.

A further embodiment of the present invention is a method of making (all-rac)-α-tocopherol having the steps of reacting trimethylhydroquinone diacetate (TMHQ-DA) with a lipase to form trimethylhydroquinone-1-monoacetate (TMHQ-1-MA), reacting the TMHQ-1-MA with isophytol or an equivalent thereof to form (all-rac)-α-tocopherol acetate, and deacetylating the (all-rac)-α-tocopherol acetate to form (all-rac)-α-tocopherol.

DETAILED DESCRIPTION OF THE INVENTION

It has now been found that TMHQ-DA can be absolutely regioselectively converted into TMHQ-1-MA by subjecting the TMHQ-DA to an enzymatic monosaponification by means of a lipase.

One embodiment of the present invention is a process for converting trimethylhydroquinone diacetate (TMHQ-DA) into trimethylhydroquinone-1-mono-acetate (TMHO-1-MA) by contacting TMHQ-DA with a lipase to effect an enzymatic monosaponification of the TMHQ-DA.

In a preferred embodiment of the present invention the lipase is immobilised on a solid carrier material. Said carrier material can be a hydrophobic carrier, e.g. a polypropylene carrier such as ACCURELO® MP1001, (Membrana GmbH, Obernburg, Germany). A carrier of a different nature, namely the alkaline catalyst carrier CELITE® (chemical composition: 87% $SiO_2$, 0.9% CaO, 6.1% $Al_2O_3$, 1.6% $Fe_2O_3$, 1.6% $Na_2O+K_2O$; pH (10% suspension, 25° C.) =8.5) which is often used for the immobilization of enzymes, did not give a satisfying performance of the immobilized enzyme, however.

Lipases which are suitable for the purposes of the present invention include those belonging to enzyme class EC 3.1.1.3.

Among the various lipases which are available on the market the following, in particular, have proved to be particularly efficient for the purposes of the present invention: *Thermomyces lanuginosus* lipase (TLL); *Mucor mihei* lipase (MML); Alcaligenes spec. lipase (ASL); *Candida rugosa* lipase (CRL); *Candida antartica* (fraction B) lipase (CAL(B)); and Pseudomonas spec. lipase (PSL), e.g. *Pseudomonas fluorescens* lipase (PFL). Preferred lipases are PSL, PFL and TLL; with TLL being particularly preferred.

The enzymatic monosaponification of the invention is conveniently carried out in a hydrophobic solvent, e.g. in 1-methyl-2-pyrrolidone or, particularly, in an ether solvent such as tert.-butyl methyl ether, butyl ether, methyl 2-methyl-2-butyl ether or the like, or mixtures thereof, with tert.-butyl methyl ether being particularly preferred.

Conveniently from about 0.01 to about 99.5 vol %, preferably about 0.03 to about 20 vol %, more preferably about 0.09 to about 5 vol % of water or buffer, such as phosphate buffer, may be added to the ether solvent. Ethanol may be present in a concentration of up to 1%.

Tetrahedron 56 (2000) 317–321 describes, inter alia, the selective monosaponification of 2-methyl-1,4-diacetoxynaphthalene into the corresponding 1-acetoxy-4-hydroxy compound by means of the free enzyme PSL in tert.-butyl methyl ether in the presence of water. When repeating this experiment over a time up to 185 hours it was found, however, that inconsistent results were obtained. Furthermore, when treating TMHQ-DA with the free enzyme PSL under the same reaction conditions over a time of up to about 300 hours, the initial reaction rate was only about one third. As against that the monosaponification of TMHQ-DA by means of immobilized PSL over a time of <100 hours resulted in an almost quantitative conversion, and similar results were obtained with immobilized PFL and immobilized TLL.

The reaction rate of the monosaponification of the present invention normally increases with increased reaction temperatures. The maximum temperature is, of course, limited by the boiling point of the solvent (55° C. in the case of tert.-butyl methyl ether) but still higher temperatures can be achieved when performing the enzymatic monosaponification under pressure. With respect to some of the lipases, particularly TLL, the temperature may be raised up to about 60 to about 80° C.

The enzymatic monosaponification of the invention is thus conveniently carried out in a temperature range of from about 4 to about 80° C., preferably in the range of from about 20 to about 75° C.

The ratio of enzyme, both free and immobilized, to the substrate (TMHQ-DA) can vary in a rather broad range, conveniently of from about 0.001 g/g to about 10 g/g, preferably from about 0.01 to about 0.2 g/g.

The ratio of the substrate (TMHQ-DA) to the solvent can likewise vary in a rather broad range, conveniently of from about 0.001 g/g to about 100 g/g, preferably from about 0.01 g/g to about 0.8 g/g.

When the enzyme is immobilized on an appropriate carrier the monosaponification of the invention may be performed continuously, e.g. in a fixed-bed reactor or a continuous stirred tank reactor, instead of batch-wise.

As mentioned earlier, the TMHQ-1-MA obtained by the enzymatic monosaponification of the invention can be converted into (all-rac)-α-tocopheryl acetate, e.g. by reaction with isophytol. If (all-rac)-α-tocopherol should be present in the crude product, such (all-rac)-α-tocopherol can, if desired, be converted into its acetate by acetylation, e.g. by means of acetic anhydride. Another embodiment of the present invention is a method of making (all-rac)-α-tocopherol acetate by converting trimethylhydroquinone diacetate into trimethylhydroquinone-1-monoacetate by means of a lipase, and condensing the trimethylhydroquinone-1-monoacetate with isophytol or an equivalent.

Another embodiment of the present invention is a method of making (all-rac)-α-tocopherol acetate having the steps of reacting trimethylhydroquinone diacetate (TMHQ-DA) with a lipase to form trimethylhydroquinone-1-monoacetate (TMHQ-1-MA), followed by reacting the TMHQ-1-MA with isophytol or an equivalent thereof to form (all-rac)-α-tocopherol acetate.

A further embodiment of the present invention is a method of making (all-rac)-α-tocopherol having the steps of reacting trimethylhydroquinone diacetate (TMHQ-DA) with a lipase to form trimethylhydroquinone-1-monoacetate (TMHQ-1-MA), reacting the TMHQ-1-MA with isophytol or an equivalent thereof to form (all-rac)-α-tocopherol acetate, and deacetylating the (all-rac)-α-tocopherol acetate to form (all-rac)-α-tocopherol.

The following examples are provided to further illustrate the process of the present invention. These examples are illustrative only and are not intended to limit the scope of the invention in any way.

EXAMPLES

Example 1

Batch Experiments in Glass Vessels Using Free Lipases 5 ml of tert.-butyl methyl ether, 50 μl of water, 1.67 mg free enzyme (lipases were from Fluka Chemie AG (Buchs, Switzerland)) and 80 mg TMHQ-DA (crude, i.e. material which resulted from rearrangement-aromatization of ketoiso-phorone and consisted of about 90% TMHQ-DA and about 9% of trimethyl-catechol diacetate (TMC-DA)) were added into a vessel. The headspace of the vessel was flushed with nitrogen. The vessel was placed into an incubator at 50° C. and stirred at 700 rpm to ensure good mixing. To take samples, the vessels were opened, 500 μl were taken out, the headspace was flushed with nitrogen and the vessel was closed again. The sample was then diluted to a substrate or product concentration of 0.5–1.0 wt % and analyzed by GC.

TABLE 1

Conversion for various lipases and TLL after 6, 12, 24 or 48 h, respectively (E/S = 1/48, $C_{TMHQ-DA}$ = 0.019 g/g)

| | Conversion X (%) | |
|---|---|---|
| Time (h) | PFL | TLL |
| 6 | 5 | 5 |
| 12 | 47 | 6 |
| 24 | 61 | 12 |
| 48 | 74 | 19 |

Example 2

Batch Experiments Using Immobilized Enzymes

The carriers provided by Membrana GmbH Obernburg under the name ACCUREL® MP1001 have a size of 400–1000 μm. Before the immobilization carrier particles with a size of 1000 μm were selected by sieving.

For the immobilization, 500 mg of ACCUREL® MP1001 in 1.7 ml of ethanol and 100 mg of lipase powder, dissolved in 2.5 ml of potassium phosphate buffer ($KH_2PO_4$, pH 7, 20 mM), were mixed and shaken overnight in a shaker at room temperature. The immobilized lipase was collected by filtration, washed three times with the same buffer and dried at room temperature for a few hours. The immobilized enzyme was stored at 4° C. until use.

The amount of protein immobilized was determined using a modified Lowry method.

10 of tert.-butyl methyl ether, 100 μl of water, 20 mg of immobilized enzyme (13% enzyme/87% of ACCUREL carrier) (the lipases were part of a screening kit provided by Roche Diagnostics GmbH (Mannheim, Germany) called "Chirazyme") and 160 mg of TMHQ-DA were added into a vessel. The head-space of the vessel was flushed with nitrogen. The vessel was placed into an incubator at 33° C. and stirred at 700 rpm to ensure good mixing. To take samples, the vessels were opened, 500 μl were taken out, the headspace was flushed with nitrogen and the vessel was closed again. The sample was then diluted to a substrate or product concentration of 0.5–1.0 wt % and analyzed by GC.

TABLE 2

Conversion of pure TMHQ-DA using chirazymes after 96 h ($E_l/S$ = 1/8, $C_{TMHQ-DA}$ = 0.019 g/g)

| Lipase | Source | Conversion X (%) |
|---|---|---|
| CAL (B) | Candida antarctica (fraction B) | 70,0 |
| CRL | Candida rugosa | 65.0 |
| CRL (pure) | Candida rugosa (purified) | 87.0 |
| CAL (A) | Candida antarctica (fraction A) | 0.7 |
| PSL | Pseudomonas spec. | 96.1 |
| HPL | Hog pancreas | 5.0 |
| TLL | Thermomyces lanuginosus | 100.0 |
| MML | Mucor mihei | 18.0 |
| ASL | Alcaligenes spec. | 24.0 |
| HL1 (esterase) | Hog liver (fraction 1) | 0.2 |

Use of crude TMHQ-DA (see Example 1) resulted in a relative conversion rate in the range of from 95% to 100% as compared to use of pure TMHQ-DA.

TABLE 3

Comparison between immobilized PSL and TLL ($E_1/S = \frac{1}{2}$, $C_{TMHQ-DA} = 0.014$ g/g, temperature: 50° C., other conditions see above, selectivity >99.5% for both enzymes)

| Time (h) | Conversion X (%) | |
|---|---|---|
| | PSL | TLL |
| 6 | 10 | 93 |
| 12 | 20 | 99 |
| 24 | 37 | 99 |

Example 3

Continuous Enzymatic Saponification in a Fixed-bed Reactor

Continuous saponification of TMHQ-DA to TMHQ-1-MA was carried out in a fixed-bed reactor (900 mg TLL immobilized on ACCUREL® MP1001; height of bed: 73 mm; diameter of bed: 12.0 mm; bed density: 0.11 g/ml; bed volume: 8.1 ml carrier diameter: 0.7 mm) at 40° C., substrate flow: TMHQ-DA in a concentration of 0.01 g/g in water-saturated tert.-butyl methyl ether; mass flow of tert.-butyl ether=0.080 mg/min; and mass flow of TMHQ-DA=0.85 g/d.

The immobilized TLL was stable and active for at least 224 hours; the selectivity of the TLL in the saponification of TMHQ-DA to TMHQ-1-MA was almost 100 at 100% conversion; and even at long residence times or when feeding a TMHQ-DA solution having a low concentration, saponification of TMHQ-1-MA to TMHQ did only occur at a rate of less than 0.1%.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for converting trimethylhydroquinone diacetate (TMHQ-DA) into trimethylhydroquinone-1-monoacetate (TMHQ-1-MA) comprising contacting TMHQ-DA with a lipase to effect an enzymatic monosaponification of the TMHQ-DA, wherein the lipase is immobilized on a solid carrier material.

2. A process according to claim 1 wherein the lipase is Pseudomonas species lipase.

3. A process according to claim 2 wherein the lipase is *Pseudomonas fluorescens* lipase.

4. A process according to claim 1 wherein the lipase is *Thermomyces lanuginosus* lipase.

5. A process according to claim 1 wherein the enzymatic monosaponification is carried out in a hydrophobic solvent.

6. A process according to claim 5 wherein the solvent is tert-butyl methyl ether.

7. A process according to claim 1 wherein the enzymatic monosaponification is carried out continuously.

* * * * *